(12) United States Patent
Alster et al.

(10) Patent No.: US 7,665,847 B2
(45) Date of Patent: Feb. 23, 2010

(54) EYE MAPPING

(75) Inventors: Yair Alster, Tel-Aviv (IL); Omer Rafaeli, Tel-Aviv (IL); Edward Elikhis, Raanana (IL)

(73) Assignee: Reichert, Inc., Depew, NY (US)

( * ) Notice: Subject to any disclaimer, the term of this patent is extended or adjusted under 35 U.S.C. 154(b) by 0 days.

(21) Appl. No.: 10/556,146

(22) PCT Filed: May 5, 2004

(86) PCT No.: PCT/IL2004/000374

§ 371 (c)(1),
(2), (4) Date: Jan. 18, 2007

(87) PCT Pub. No.: WO2004/098447

PCT Pub. Date: Nov. 18, 2004

(65) Prior Publication Data

US 2007/0121070 A1    May 31, 2007

Related U.S. Application Data

(63) Continuation-in-part of application No. 10/398,375, filed as application No. PCT/IL01/00933 on Oct. 7, 2001, which is a continuation-in-part of application No. 09/781,548, filed on Feb. 13, 2001, application No. 10/556,146, which is a continuation-in-part of application No. 10/368,002, filed on Feb. 19, 2003.

(60) Provisional application No. 60/467,562, filed on May 5, 2003, provisional application No. 60/357,115, filed on Feb. 19, 2002.

(51) Int. Cl.
*A61B 3/10* (2006.01)
(52) U.S. Cl. ........................ 351/224; 351/205; 351/221
(58) Field of Classification Search ......... 351/205–206, 351/210, 221–226
See application file for complete search history.

(56) References Cited

U.S. PATENT DOCUMENTS

| 3,883,235 A | * | 5/1975 | Lynn et al. .................. 351/246 |
| 4,349,250 A | | 9/1982 | Gelius |
| 4,634,243 A | | 1/1987 | Massof et al. |

(Continued)

FOREIGN PATENT DOCUMENTS

| WO | WO 02/28266 | 4/2002 |
| WO | WO 03/028534 | 4/2003 |

OTHER PUBLICATIONS

Jay M. Enoch et al., "Hyperacuity Perimetry: Assessment of Macular Function Through Ocular Opacities", Arch Ophtalmol, vol. 102(8), Aug. 1984, pp. 1164-1168.

(Continued)

*Primary Examiner*—Scott J Sugarman
*Assistant Examiner*—Dawayne A Pinkney
(74) *Attorney, Agent, or Firm*—Hodgson Russ LLP

(57) ABSTRACT

A method of providing an eye diagnosis. The method includes displaying stimuli to a patient, receiving indications of locations in which the stimuli were perceived by the patient, analyzing the spatial relationship between at least some of the received indicated locations and classifying the patient with regard to a retinal related disease, at least partially based on the spatial analysis.

97 Claims, 5 Drawing Sheets

U.S. PATENT DOCUMENTS

| | | | |
|---|---|---|---|
| 4,798,456 | A | 1/1989 | Enoch et al. |
| 4,822,162 | A | 4/1989 | Richardson et al. |
| 4,995,717 | A | 2/1991 | Damato |
| 5,061,060 | A | 10/1991 | Aulhorn et al. |
| 5,412,561 | A | 5/1995 | Rosensheim et al. |
| 5,463,431 | A * | 10/1995 | Suzuki et al. ............... 351/226 |
| 5,506,633 | A | 4/1996 | Sperling |
| 5,539,482 | A | 7/1996 | James et al. |
| 5,565,949 | A | 10/1996 | Kasha, Jr. |
| 5,589,897 | A | 12/1996 | Sinclair et al. |
| 5,864,384 | A | 1/1999 | McClure et al. |
| 5,883,692 | A | 3/1999 | Agonis et al. |
| 5,892,570 | A | 4/1999 | Stevens |
| 5,946,075 | A | 8/1999 | Horn |
| 6,027,217 | A | 2/2000 | McClure et al. |
| 6,033,076 | A | 3/2000 | Braeuning et al. |
| 6,260,970 | B1 | 7/2001 | Horn |
| 6,406,437 | B1 | 6/2002 | Zur et al. |
| 6,494,578 | B1 | 12/2002 | Plummer et al. |
| 6,513,931 | B1 | 2/2003 | Torrey et al. |
| 6,520,640 | B1 | 2/2003 | Binnun |
| 6,527,391 | B1 | 3/2003 | Heijl et al. |
| 6,572,229 | B2 | 6/2003 | Wei |
| 6,578,966 | B2 | 6/2003 | Fink et al. |
| 6,585,376 | B1 | 7/2003 | Matsumoto |
| 6,688,746 | B2 | 2/2004 | Malov |
| 6,742,894 | B2 | 6/2004 | Stewart |
| 2002/0024634 | A1 * | 2/2002 | Fink et al. ................... 351/237 |
| 2002/0042580 | A1 | 4/2002 | Alster et al. |
| 2003/0036907 | A1 | 2/2003 | Stewart et al. |
| 2003/0081176 | A1 * | 5/2003 | Stewart ...................... 351/223 |
| 2005/0122477 | A1 * | 6/2005 | Alster et al. ................ 351/237 |

OTHER PUBLICATIONS

Michael Wall and Alfredo A. Sadun, "Threshold Amsler Grid Testing: Cross-Polarizing Lenses Enhance Yield" Arch Ophthalmol, vol. 104(4), Apr. 1986, pp. 520-523.

Stuart L. Fine and The Macular Photocoagulation Study Group, "Early Detection of Extrafoveal Neovascular Membranes by Daily Central Field Evaluation", Ophthalmol. 92(5), May 1985, pp. 603-609.

Vasudevan Lakshminarayanan et al., "Quantifications of Metamorphosia Using Hyperacuity Techniques", Optometry and Vision Science, vol. 68, No. 12, Dec. 1991, pp. 942-945.

Michael J. Tolentino et al. "Visual Field Deficits in Early Age-Related Macular Degeneration", Vision Res., vol. 34, No. 3, pp. 409-413, Feb. 1994.

Reginald G. Ariyasu et al., "Sensitivity, Specificity and Predictive Values of Screening Tests for Eye Conditions in a Clinic-Based Population", Ophthalmology, vol. 103, No. 11, Nov. 1996, pp. 1751-1760.

Michael L. Slavin, "The Use of the Red Amsler Grid and Red-Green Lenses in Detecting Spurious Paracentral Visual Fields Defects", American Journal of Ophthalmology, vol. 103, No. 3, Part 1, Mar. 1987, pp. 338-339.

Michael Wall and Donald R. May, "Threshold Amsler Grid Testing in Maculopathies", Ophthalmol. 94(9), Sep. 1987, pp. 1126-1133.

* cited by examiner

EYE MAPPING

RELATED APPLICATIONS

This application is a U.S. national filing of PCT Application No. PCT/IL2004/000374, filed on May 5, 2004. This application also claims the benefit of U.S. provisional patent application 60/467,562, filed May 5, 2003, the disclosure of which are incorporated herein by reference. PCT/IL2004/000374 is also a continuation in part of U.S. patent application Ser. No. 10/398,375, filed on Oct. 20, 2003, published as US 2004-0075814, which is a national phase of PCT application PCT/IL01/00933, filed on Oct. 7, 2001, published as WO 02/28266, which takes priority from U.S. patent application Ser. No. 09/781,548, filed on Feb. 13, 2001, issued as U.S. Pat. No. 6,656,131. The present application is also a continuation in part of U.S. patent application Ser. No. 10/368,002, filed on Feb. 19, 2003, published as US 2003-0223038 A1, which claims the benefit of U.S. provisional patent application 60/357,115, filed on Feb. 19, 2002 corresponds to PCT patent application PCT/IL03/00135, filed on Feb. 19, 2003, published as WO 03/070089, the disclosures of all of which are incorporated herein by reference.

FIELD OF THE INVENTION

The present invention relates to the field of eye tests and particularly to tests for mapping the visual field of patients.

BACKGROUND OF THE INVENTION

Age related Macular degeneration (AMD) is the leading cause of blindness among people over 50 in the western world. At the moment there is no cure for advanced AMD, but the progression of an exudative (wet) type of AMD can be slowed or even stopped by various evolving treatment methods. Earlier diagnosis allows for better chances of treatment success.

Various methods have been described for AMD diagnosis. U.S. Pat. No. 6,406,437 to Zur et al., the disclosure of which is incorporated herein by reference, describes a diagnosis method based on transmission of light beams at different positions on a patients eye and receiving feedback on whether the beams were detected. The method uses an LCD projector coupled to a portable computer.

U.S. Pat. No. 5,589,897 to Sinclair et al., the disclosure of which is incorporated herein by reference, describes a method of testing vision field of patients in order to enhance images displayed to the individuals. The method determines effects of contrast, sensitivity and distortion in the visual field of the patient.

U.S. Pat. No. 6,572,229 to Wei, the disclosure of which is incorporated herein by reference, describes a visual field tester for disease diagnosis.

U.S. Pat. No. 6,260,970 to Horn, the disclosure of which is incorporated herein by reference, describes a method for detecting a glaucoma or a diabetic eye disease. The method includes fixating a patient's eye at a central point and displaying marks of same size and shape but different hue. The patient indicates whether the marks were identified, and accordingly an eye map is generated. The map includes a value for each point at which marks were presented.

U.S. patent publication 2002/0042580 to Alster Yair et al., the disclosure of which is incorporated herein by reference, describes a diagnosis method which is based on patient input responsive to distortions in displayed patterns.

SUMMARY OF THE INVENTION

An aspect of some embodiments of the invention relates to classifying a patient as to existence and/or a stage of a retinal related disease based on spatial analysis of patient input indications of the perceived locations of displayed stimuli.

Using spatial analysis of the patient input can provide, in some cases, better information on the state of the patient than quantative information on the number of indications relating to a disease provided by the patient. In some embodiments of the invention, the spatial analysis comprises generating a map representative of the visual field of the patient and analyzing the map.

Optionally, the map analysis includes identifying on the map clusters having values that are indicative of afflicted tissue. In some embodiments of the invention, the map analysis includes determining the size, shape and/or other parameters of one or more clusters on the map. Alternatively or additionally, the spatial analysis includes comparison of scores determined for different areas of the visual field of the patient. In addition to automatically analyzing the map by a computer, based on a predetermined algorithm, the map may be displayed to a physician for analysis.

Optionally, the classification includes determining whether the patient has CNV. Alternatively or additionally, classification includes determining whether the patient has any other specific chorio-retinal disease, such as AMD or myopia. Further alternatively or additionally, the classification includes determining whether the patient has any specific choroidal or retinal disease. Further alternatively or additionally, the classification includes determining whether the patient has any of a plurality of retinal-related diseases and/or has a retinal-related disease stage. Further alternatively or additionally, the classification includes determining a stage of a specific disease, such as whether the patient has a dry or wet AMD or whether the patient has an intermediate AMD stage or a CNV AMD stage. Further alternatively or additionally, the classification determines whether the stage of a patient's disease has changed significantly between test sessions and/or has changed significantly after a treatment session. In some embodiments of the invention, the classification includes determining whether the stage of a patient's eye disease is improving or deteriorating. In the following description and claims, the term retinal related diseases includes retinal diseases, chorio-retinal diseases (e.g., AMD and myopia) and choroidal diseases.

In some embodiments of the invention, the displayed stimuli include markings of substantially any shape, such as squares, circles or diamonds. Alternatively, the displayed stimuli include defects in displayed patterns, such as gaps (missing portions) in patterns, shape distortions (e.g., a dent in a straight line or a bump in a circle or spiral). Alternatively or additionally, the stimuli defects include a color change in the pattern and/or a blurring of the pattern.

Optionally, the displayed stimuli include stimulus with various amplitude (i.e., various levels of detection probability). The amplitude variations are optionally controlled by changing the length of gaps and/or shape distortions. In some embodiments of the invention, the amplitude variations are controlled by changing the brightness, contrast, shape size and/or color of the displayed stimuli.

An aspect of some embodiments of the invention relates to classifying a patient as to existence and/or a stage of a retinal related disease based on a visual field map generated based on patient input not primarily relying on signal contrast. In some embodiments of the invention, the patient input is based on the shapes of displayed patterns. The patient input may include an indication on whether a displayed shape is rectangular or round, whether a distortion is perceived and/or the location of a perceived shape distortion or other defect.

In many AMD patients, the pathology of the disease manifests in identifying pattern defects where no such defects exist. By mapping the reported locations of the identified defects, a map of the visual field of the patient showing the AMD afflicted areas is achieved. It is noted that some retinal related diseases do not manifest, at least in early stages, in lack of detection of signals. Also, the use of displayed patterns provides information with which the patient indications may be verified.

In some of these embodiments, the patient indications include for each pattern an indication of whether the pattern shape (e.g., a gap, a distortion) was identified. The positions of stimulus not identified by the patient are assumed to represent retina-related pathologies. Some stimulus may not be identified by the patient due to low sensitivity of the patient's vision. In some embodiments of the invention, stimuli not identified due to low sensitivity are weeded out. Optionally, when signals of an amplitude level are not identified (or are identified with a low probability) regardless of their location on the patient's visual field, the non-identification of these signals are not assumed to represent retina-related pathologies.

It is noted that in some embodiments of the invention, the stimuli displayed to the patient do not need to be in a large number of different contrast levels. In some embodiments of the invention, all the displayed stimuli are in substantially the same contrast (or brightness) level. Using a single contrast level (which is optionally the maximal useable contrast level) minimizes the dependence of the test on environment lighting. Also, inability to detect low brightness levels may be due to old age and/or media opacity and not due to retina-related diseases.

In some embodiments of the invention, the displayed stimuli include distortions in patterns. The patient indications indicate the locations of the distortions as perceived by the patient. When the patient indicates a position close to the displayed defect, the patient is assumed to have identified the distortion and no pathology is identified. In some embodiments of the invention, when the patient indicates a position relatively far from the actual displayed distortion, the location indicated by the patient is assumed to correspond to a lesion on the patient's eye, and not to the displayed distortion.

An aspect of some embodiments of the invention relates to generating a map of a patient visual field based on functional information from patient tests. The patient tests include displaying stimuli, each stimulus associated with a contrast level, and receiving indications responsive to the displayed stimuli. For each patient response, a contribution value for one or more pixels of the map is generated. The contribution values may have any of a plurality of values from a scale including more possible values than the number of contrast levels associated with all the stimuli.

In some embodiments of the invention, all the displayed stimuli have a same brightness level. Optionally, all the displayed stimuli have the same absolute brightness level. Alternatively or additionally, all the displayed stimuli have the same relative brightness level as compared to their surroundings (i.e., the same contrast).

An aspect of some embodiments of the invention relates to classifying a patient visual field (for example, the existence and/or a stage of a retinal-related disease) based on analysis of clusters on a functional map of the visual field. In an exemplary embodiment of the invention, the functional map is generated from a plurality of patient indications in response to stimuli. Optionally, the cluster analysis includes determining a size and/or shape of a largest cluster. In some embodiments of the invention, the cluster size is determined as a sum of the pixel values of substantially all the pixels included in the cluster. Alternatively, the sum does not include 5-10% of the pixels having lowest values. The pixel values are optionally indicative of the confidence that the corresponding area of the visual field is covered by a lesion and/or of the severity of the lesion at the area corresponding to the pixel. Alternatively, the cluster size is determined using other size definitions, such as the area of the cluster.

In some embodiments of the invention, the largest cluster is selected based on the same measure as used in determining the size of the cluster for analysis. Alternatively, the largest cluster is selected using a different size measure than the size measure used for analysis.

In some embodiments of the invention, the patient is classified based on the value of a single cluster parameter determined from the map, for example the area or intensity of the largest cluster. Alternatively, the patient is classified based on a plurality of different cluster parameters.

An aspect of some embodiments of the invention relates to classifying a patient as to existence of a retinal-related disease based on input indications actively provided by a patient. The classification applies different algorithms to the different eyes (e.g., right and left eyes and/or first and second tested in single session) of the patient. It has been found by the inventors of the present invention that the indications of the patient regarding the view from different eyes having same lesions are different and therefore it is possible to achieve better classifications using different algorithms for each eye. Optionally, the algorithms for different eyes differ in a threshold to which parameters determined for the eyes are compared.

An aspect of some embodiments of the invention relates to generating a map of the visual field of a patient's eye based on indications received from a patient. The patient indications generally correspond to positions on the map, but are spatially processed and/or their amplitudes are processed before they are used in generation of the map. In some embodiments of the invention, at least some of the patient indications affect positions on the map other than positions corresponding to the patient indications.

In some embodiments of the invention, at least some of the patient indications are spread to affect a plurality of neighboring pixels on the map. In accordance with some embodiments of the invention, the indications are received as point indications for convenience of the patients, although the displayed stimuli to which the indications relate, and/or the lesion's effect on the patient's visual field, cover areas of the visual field corresponding to a plurality of pixels. The spreading of the indications better reflects the nature of the stimuli viewed by the patient and represented by the indications. In some embodiments of the invention, at least some of the patient indications are spread out to reflect an uncertainty in the spatial location of the received indications. Optionally, the extent to which indications are spread-out, if at all, depends on the level of certainty that the indications correspond to a lesion.

The size and/or shape of the spreading optionally depends on the amplitude of the stimulus displayed to the patient, which relates to the amplitude of the lesion on the patient's visual field. Alternatively or additionally, the patient indicates an amplitude at which the stimulus was perceived and the spreading is determined responsive to the patient's indication.

In an exemplary embodiment of the invention, patient input is corrected for certainty, for example, by multiplication by a value smaller than 1 for less-certain results. Optionally, the certainty of results is determined according to the distance between a possible stimulus inducing the patient indication and the location of the indication. Alternatively or additionally, the certainty of results is determined based on inconsistency of results in certain areas and/or the response time of the patient. In some embodiments of the invention, the patient may enter more than one indication in response to a stimulus.

In some embodiments of the invention, the locations corresponding to the indications are spatially transformed in order to correct for persistent or other errors in the patient's pointing behavior and/or spatial perception. The correction of the persistent errors is optionally performed in a manner which preserves the relative locations of the patient indications. Optionally, an affine transform is used. Alternatively, a transform which stretches or condenses indications in specific regions, for example, of less or more value, is used. Further alternatively, a rotational transformation is used for correction. Optionally, a transform which minimizes an error magnitude is used.

The persistent errors are optionally determined from data collected during the test session. Alternatively or additionally, the persistent errors are determined at least partially using data collected before the test session. In an exemplary embodiment of the invention, the persistent errors are determined based on data from previous test sessions. Optionally, a first set of indications location's errors are used to generate a correction function or map for later points. Alternatively, a post-hoc analysis or an ad-hoc analysis is carried out, for example on an indication by indication basis or on groups of indications.

In an exemplary embodiment of the invention, in which the patient is requested to indicate locations of perceived distortions, the positions of patient indications of patterns in known locations are analyzed to determine a correction to be used for correcting locations of patient indications of unknown locations (e.g., patient indications corresponding to lesions reflecting on the patient's visual field).

An aspect of some embodiments of the invention relates to determining an eye treatment suggestion based on comparison of results of a plurality of functional test sessions of an eye. A plurality of test sessions in which the patient responds to displayed stimuli are performed and results of the sessions are optionally compared to determine whether treatment is required, to predict a best time for performing treatment and/or to suggest a treatment method to be used. In some embodiments of the invention, the test results are fit into a model of disease progression and accordingly the next treatment time is determined. Optionally, the test results fit into the model include a cluster parameter, such as a size of a largest cluster, the number of clusters, the accumulative size of some or all the clusters (e.g., clusters larger than a predetermined threshold). Alternatively, the location of the largest cluster is fit into the model. For example, the map may be divided into a plurality of sectors and the location of the cluster is stated by stating the clusters at least partially covered by the cluster. Further alternatively or additionally, the shape of one or more clusters and/or the location of one or more clusters, are used in determining suggested treatment.

In an exemplary embodiment of the invention, the treatment is for a CNV secondary to AMD, for example a PDT treatment. Alternatively, the treatment is for other diseases, such as CNV secondary to other diseases, such as myopia.

The model used optionally assumes that the state of the patient's visual field improves monotonously until a peak point and then begins to decrease again. The treatment is optionally set to be performed when the peak point is reached.

An aspect of some embodiments of the invention relates to combining a functional eye map based on user input with at least one other eye map, for example, by overlaying the maps. Optionally, the at least one other map comprises a physical image. Alternatively or additionally, the at least one other map comprises a functional eye map. Displaying the maps overlaid on each other is optionally used for evaluating the patient's eye disease stage. Optionally, the functional map is distorted to match the image-based map.

There is therefore provided in accordance with an exemplary embodiment of the invention, a method of providing an eye diagnosis, comprising displaying stimuli, each having an associated contrast level, to a patient, receiving indications from a patient responsive to the displayed stimuli, determining for each received indication a contribution to the pixels of a map, responsive to the displayed stimuli, wherein the contributions have a greater number of possible values, than the number of different contrast levels associated with the displayed stimuli, generating a map of the patient's visual field, responsive to the determined contributions and classifying the patient with regard to a retinal related disease, at least partially based on an analysis of the generated map.

Optionally, all the displayed stimuli have a same associated contrast level. Alternatively, the displayed stimuli have a plurality of different shapes.

Optionally, displaying the stimuli comprises displaying patterns with defects and wherein the received indications represent positions at which the patient believes to have identified the defects.

Optionally, generating the map comprises determining, for each indication, a distance between the indication and the respective displayed defect and determining a weight of specific indications in the spatial analysis according to the distance between the indications and the displayed defects. Optionally, displaying the patterns with defects comprises displaying defects of different sizes and giving higher weight to indications corresponding to larger defects. Optionally, the defects comprise spatial distortions or gaps of missing portions of the patterns. Optionally, displaying the stimuli comprises displaying patterns and wherein the received indications represent positions at which the patient believes to have identified the patterns. Optionally, generating the map comprises generating such that at least some of the indications affect pixels of the map other than the pixel corresponding to the received indication. Optionally, generating the map comprises generating such that at least some of the indications affect an area of the map larger than the area covered by the indication.

Optionally, generating the map comprises generating such that at least some of the indications affect a plurality of pixels on the map.

Optionally, generating the map comprises assigning each pixel a value at least partially representative of a severity of the malfunctioning of a corresponding area of the patient's visual field. Optionally, generating the map comprises assigning each pixel a value at least partially representative of a probability that a corresponding area of the patient's visual field is abnormal. Optionally, the method includes determining on the generated map at least one cluster of values corresponding to abnormal tissue. Optionally, the at least one cluster comprises a plurality of clusters and comprising determining a largest cluster of the plurality of clusters. Optionally, the method includes determining a parameter of the largest cluster.

Optionally, determining the parameter of the largest cluster comprises determining a size-related parameter different from a parameter used in selecting the largest cluster. Optionally, determining the parameter of the largest cluster comprises determining a size-related parameter used in selecting the largest cluster.

Optionally, determining the parameter comprises determining a plurality of parameters. Optionally, the method includes determining a parameter of the at least one cluster. Optionally, the method includes determining an area of the at least one cluster. Optionally, classifying the patient comprises providing an indication as to whether the patient has a chorio-retinal disease. Optionally, classifying the patient comprises providing an indication as to whether the patient has age related macular degeneration. Optionally, classifying the patient comprises providing an indication as to a stage of age related macular degeneration that the patient has. Optionally, the method includes displaying the map. Optionally, the determined contributions may all be zero for one or more of the indications.

There is further provided in accordance with an exemplary embodiment of the invention, an apparatus for eye diagnosis, comprising a display unit for projecting stimuli on a patient retina, each stimulus having an associated contrast level, an input interface for receiving indications from a patient responsive to the displayed stimuli, a processor adapted to generate a map of the patient's visual field, responsive to the displayed stimuli, wherein the map has a greater number of possible values for each pixel, than the number of different contrast levels associated with the displayed stimuli, and to classify the patient with regard to a retinal-related disease, at least partially based on the spatial analysis; and an output interface for providing a human tangible indication regarding the chorial-retinal disease in the patient.

Optionally, the display unit comprises a screen for displaying stimuli to a patient.

Optionally, the display unit comprises an eye projector for displaying stimulus on a patient's eye. Optionally, the processor adapted to analyze the spatial relationship is remote from the input interface. Optionally, the processor is adapted to generate a map of a visual field of the patient, responsive to the locations of indications received by the input interface, to determine a cluster parameter of a cluster on the map and to classify the patient with regard to an eye disease, at least partially based on the cluster parameter.

There is further provided in accordance with an exemplary embodiment of the invention, a method of providing an eye diagnosis, comprising displaying stimuli to a patient;

receiving indications from a patient responsive to the displayed stimuli;

providing an indication of the eye of the patient with which the patient viewed the displayed stimuli in receiving the indications; and classifying the patient with regard to an eye disease, using a classification method selected from a plurality of different classification methods responsive to the provided indication.

Optionally, providing the indication comprises providing the indication before displaying the stimuli. Optionally, providing the indication comprises providing the indication after displaying at least some of the stimuli. Optionally, providing the indication comprises providing the indication by the patient. Optionally, providing the indication comprises providing the indication by an apparatus performing the display in the form of an instruction to the patient. Optionally, providing the indication comprises providing an indication as to whether the eye is a right eye or a left eye. Optionally, providing the indication comprises providing an indication as to whether the tested eye is a first or second eye tested in a test session. Optionally, providing the indication comprises providing an indication as to whether the tested eye is a dominant eye of the patient. Optionally, the plurality of classification methods differ in a threshold to which a final score is compared.

There is further provided in accordance with an exemplary embodiment of the invention, a method of providing an eye diagnosis, comprising displaying stimuli to a patient;

receiving indications from a patient responsive to the displayed stimuli;

associating the received indications with locations in the visual field of the patient;

determining for each of the received indications a contribution to pixels of a visual field map, the contributions of at least one of the received indications having non-zero values for a plurality of pixels of the map; and generating a map of the visual field of the patient responsive to the determined contributions.

Optionally, determining the contributions comprises assigning, for each indication, a maximal value of the received indication to the corresponding location of the indication and assigning decreasing values to surrounding locations on the map. Optionally, the number of pixels to which a received indication relates depends on an amplitude of the displayed stimulus of the received indication. Optionally, the method includes displaying the map.

Optionally, the method includes displaying the map overlaid on at least one other map of the eye. Optionally, the method includes classifying the patient with regard to a chorio-retinal disease responsive to the map. Optionally, associating the received indications with locations in the visual field comprises associating received indications with locations of corresponding displayed stimuli. Optionally, associating the received indications with locations in the visual field comprises associating received indications with locations of the received indications. Optionally, at least some of the patient indications affect positions on the map other than positions corresponding to the patient indications.

There is further provided in accordance with an exemplary embodiment of the invention, a method of providing an eye diagnosis, comprising displaying stimuli to a patient;

receiving indications from a patient responsive to the displayed stimuli;

associating the received indications with locations in the visual field of the patient;

determining for each of the received indications a contribution to pixels of a visual field map, the contributions of at least one of the received indications relating to a translation of the associated location of the received indication due to persistent errors in the patient's perception and/or pointing behavior; and generating a map of the visual field of the patient responsive to the determined contributions.

Optionally, the persistent errors are determined responsive to indications received before or after a current test session. Alternatively, the persistent errors are determined responsive to indications received during a current test session. Optionally, the persistent errors are determined responsive to indications provided by the patient at locations close to defects of the displayed stimuli. Optionally, the transformation is achieved by applying an affine transform to the indications.

There is further provided in accordance with an exemplary embodiment of the invention, a method of providing an eye diagnosis, comprising performing a plurality of test sessions including displaying stimuli to a patient receiving indications from a patient responsive to the displayed stimuli; and determining information on the visual field of the patient responsive to the indications, comparing the determined information of the plurality of sessions; and suggesting a decision as to treatment responsive to the comparison.

Optionally, determining information on the visual field comprises generating a map of the visual field. Optionally, determining information on the visual field comprises determining a parameter of a cluster on the map of the visual field.

Optionally, suggesting a decision as to treatment comprises suggesting a time to perform treatment. Optionally, suggesting a time to perform treatment comprises suggesting a type of treatment to be used. Optionally, suggesting a decision as to treatment comprises suggesting whether to perform treatment. Optionally, suggesting a decision as to treatment comprises suggesting a decision as to treatment of a retinal-related disease.

Optionally, suggesting a decision as to treatment comprises suggesting a decision as to treatment of ADT. Optionally, comparing the determined information of the plurality of sessions comprises fitting a parameter value determined for each of the sessions into a model.

Optionally, comparing the determined information of the plurality of sessions comprises predicting a time when the parameter value reaches an extreme. Optionally, fitting the parameter value into a model comprises fitting into a parabolic model. Optionally, fitting the parameter value into a model comprises fitting a parameter related to a size or shape of a cluster on a map of the visual field.

There is further provided in accordance with an exemplary embodiment of the invention, a method of providing an eye diagnosis, comprising displaying stimuli patterns having a plurality of different shapes, to a patient, receiving indications from a patient responsive to the displayed stimuli, analyzing the spatial relationship between locations associated with the received indications; and classifying the patient with regard to a retinal related disease, at least partially based on the spatial analysis.

Optionally, displaying the stimuli comprises displaying patterns with defects and wherein the received indications represent positions at which the patient believes to have identified the defects. Optionally, analyzing the spatial relationship comprises generating a map responsive to the locations of the received indications.

Optionally, the spatial analysis comprises comparing of scores determined for different areas of the visual field of the patient. Optionally, the locations associated with the received indications comprise the locations of the received indications. Optionally, the locations associated with the received indications comprise the locations of the displayed stimulus.

There is further provided in accordance with an exemplary embodiment of the invention, a method of providing an eye diagnosis, comprising displaying stimuli to a patient, receiving indications of locations in which the stimuli were perceived by the patient, analyzing the spatial relationship between at least some of the received indicated locations; and classifying the patient with regard to a retinal related disease, at least partially based on the spatial analysis.

Optionally, displaying the stimuli comprises displaying markings and wherein the indications relate to the location of the markings. Optionally, displaying the stimuli comprises displaying markings with a plurality of different contrast levels and/or shapes. Optionally, displaying the stimuli comprises displaying distortions in patterns. Optionally, displaying the distortions comprises displaying a plurality of distortions of different sizes.

Optionally, analyzing the relationship comprises generating a map.

There is further provided in accordance with an exemplary embodiment of the invention, a method of providing an eye diagnosis, comprising displaying patterns to a patient, receiving, from the patient, indications relating to shapes of the displayed patterns as perceived by the patient generating a map of a visual field of the patient responsive to the received indications; and classifying the patient with regard to a retinal related disease, at least partially based on the spatial analysis.

Optionally, receiving indications relating to the shapes comprises receiving indications of perceived distortions in the patterns.

There is further provided in accordance with an exemplary embodiment of the invention, a method of generating a map of a visual field of a patient comprising displaying at least one stimulus, with a contrast level, receiving from a patient indications regarding the displayed stimulus; and generating a map containing a plurality of points, each point being generated from one or more indications, wherein an indication is associated with a contrast level of a displayed stimulus and wherein the average number of different contrast levels of indications used to reconstruct a point is less than 4, 3 or 2.

There is further provided in accordance with an exemplary embodiment of the invention, a method of providing an eye diagnosis, comprising displaying consecutively a plurality of stimuli to a patient, each stimulus relating to less than 20% of a mapped visual field of the patient, receiving indications from a patient responsive to the displayed stimuli;

analyzing the spatial relationship between locations associated with the received indications, so as to generate a map; and classifying the patient with regard to a retinal related disease, at least partially based on the spatial analysis.

BRIEF DESCRIPTION OF THE DRAWINGS

Particular exemplary embodiments of the invention will be described with reference to the following description of embodiments in conjunction with the figures, wherein identical structures, elements or parts which appear in more than one figure are generally labeled with a same or similar number in all the figures in which they appear, in which.

DETAILED DESCRIPTION OF EXEMPLARY EMBODIMENTS

Figure 1:
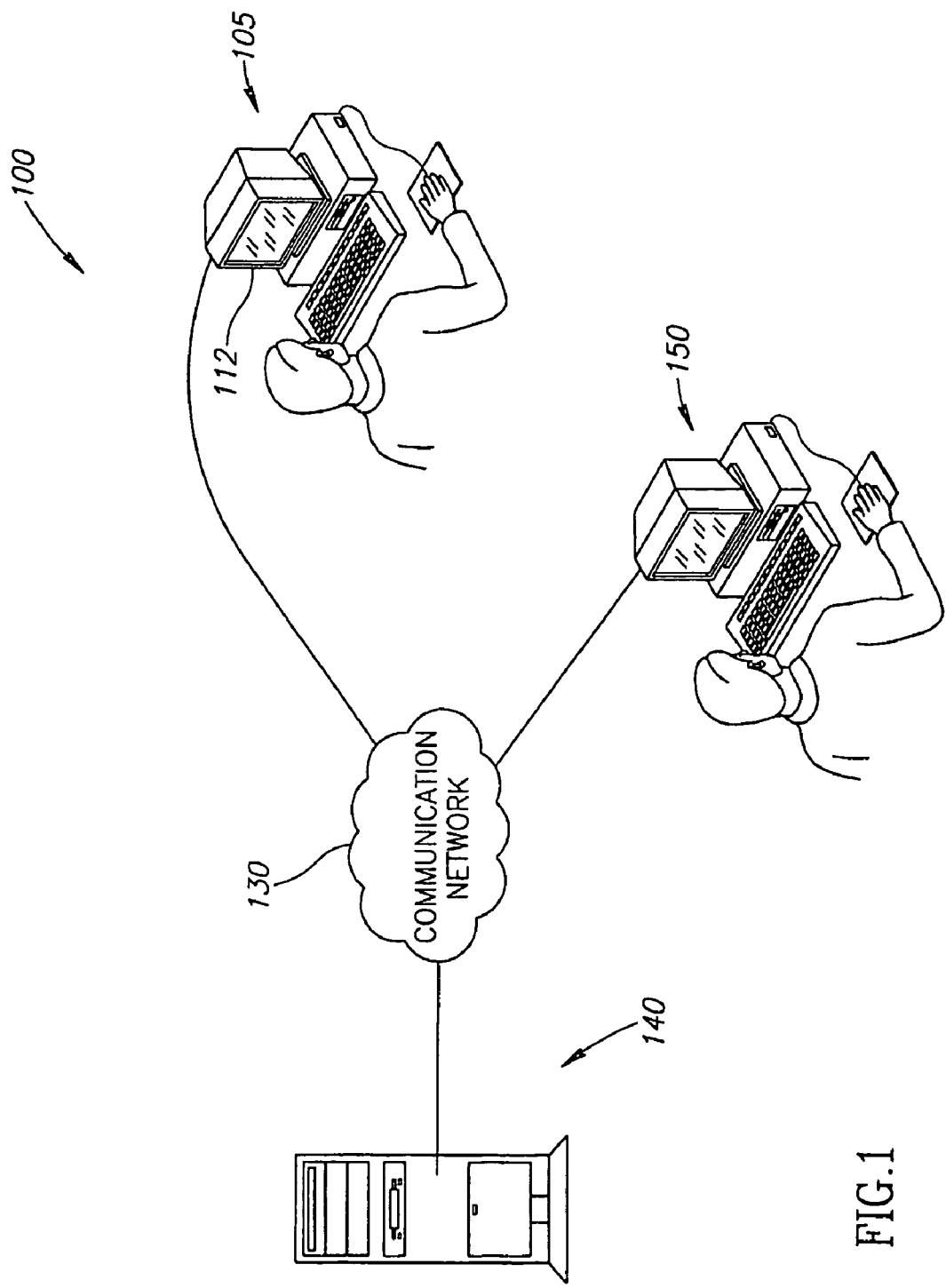
FIG. 1 is a schematic illustration of an eye diagnosis system, in accordance with an exemplary embodiment of the invention.

FIG. 1 is a schematic illustration of an eye diagnosis system 100, in accordance with an exemplary embodiment of the invention. System 100 optionally includes a user terminal 105, which may be a general purpose computer used by a patient for various tasks, or may be dedicated for eye diagnosis. Terminal 105 includes a screen 112 on which patterns are displayed and one or more input devices through which patient indications are received, such as a keyboard and/or a mouse. Alternatively or additionally, other input devices may be used, such as a touch sensitive screen and/or a joystick. A server 140 transmits instructions to user terminal 105 on the patterns to be displayed and receives user responses from user terminal 105, for example through a communication network 130, e.g., the Internet. Based on the patient responses to the displayed patterns, server 140 calculates a map of the patient's eye and/or provides a diagnosis of the patient's eye, as described below in detail. Alternatively, some or all of the calculations are performed by user terminal 105.

In some embodiments of the invention, a physician terminal 150, close to server 140 or remote therefrom, is used by a physician to view the patient's eye map and/or to control the operation software of server 140.

Although system 100 is shown as being distributed, such that user terminal 105 may be separated from server 140 by many miles, even thousands of miles, system 100 may be included in a single room and/or on a single computer, for example for patients that do not have home computers.

In some embodiments of the invention, instead of using terminal 105 other display units may be used, such as an eye projector, screens mounted on eye glasses, portable terminals or wide cinema screens.

Figure 2:
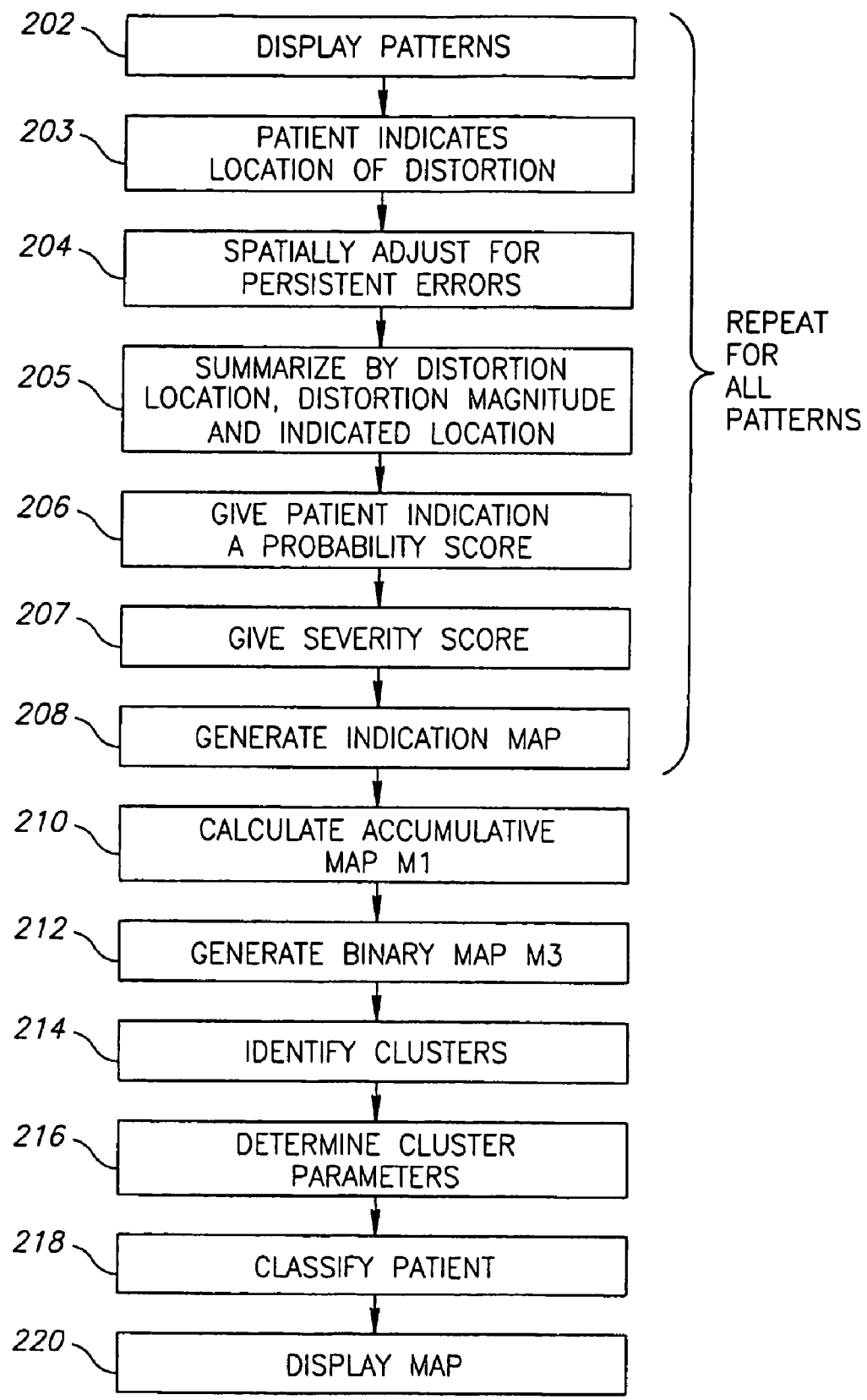
FIG. 2 is a flowchart of a mapping procedure of an eye, in accordance with an exemplary embodiment of the invention.

FIG. 2 is a flowchart of a mapping procedure of an eye, in accordance with an exemplary embodiment of the invention. Optionally, the patient performs the test procedure with one eye covered. In some embodiments of the invention, after a first eye is tested, the second eye is tested, if necessary.

In each test session, a plurality of patterns with a distortion are displayed (202) on screen 112. In some embodiments of the invention, the stimuli are displayed for short durations up to about 400 milliseconds, for example between about 100-200 milliseconds. For each displayed pattern, the patient is requested to indicate (203) the location of the distortion. The results for each pattern are optionally summarized (205) by the location of the distortion, the magnitude of the distortion and the location indicated by the patient. In some embodiments of the invention, the location indications are spatially adjusted (204) in order to correct for persistent errors in the patient's pointing, perception and/or other non-eye mechanisms. In some embodiments of the invention, a record is kept of distortions for which no response was received. The number of distortions for which patient indications were not received is optionally used in determining the reliability of the test. Alternatively or additionally, distortions for which patient indications are not received are used in evaluating the areas of the displayed distortion as the distortions may not have been perceived by the patient due to a lesion, overlying the displayed distortion, on the patient's visual field.

Each patient indication is given (206) a probability score indicative of the probability that the patient indication is indicative of impaired eye tissue and is not a correct indication of the location of the displayed distortion. Generally, if the patient indicates a position close to the actual distortion, the patient's indication is most probably indicative of healthy eye tissue as the patient identified the displayed distortion. If, however, the patient indicates a different position, the patient's eye may be impaired at the indicated location and therefore the patient did not identify the displayed distortion, which was overridden by a competing pathological stimulus caused by a retinal-related lesion. The patient indication is given (207) a severity score S, optionally as a function of the distortion size and the probability score. As the distortion is greater, the retinal lesion needs to be more severe in order to cause the patient to point in the wrong location.

For each displayed pattern, a map M2 indicative of the health of each point of the eye tissue of the patient based on the response of the patient to the displayed pattern, is generated (208). An accumulative map M1 is calculated (210) based on the maps M2 of each of the patterns. In some embodiments of the invention, a binary map M3, which indicates impaired areas on accumulative map M1, is generated (212). The binary map generally identifies (214) clusters of impaired eye tissue. Parameters of the impaired clusters are optionally determined (216) and the patient is classified (218) according to the cluster parameters. Alternatively or additionally, accumulative map M1 and/or a clustered variation thereof is displayed (220) for analysis.

Referring in detail to displaying (202) patterns on the screen, in some embodiments of the invention, in order to map the patient's visual field, patterns having distortions at different areas on the visual field are displayed to the patient. In addition, patterns with different magnitude of distortion are displayed. Each pattern is optionally represented by the location of the distortion relative to the center of the display (corresponding to the fovea) and the magnitude of the distortion.

Alternatively or additionally to displaying (202) patterns with distortions, patterns without distortions are displayed. Distortions detected by the patient in this alternative are due to imperfections in the patient's visual field, as no distortions were displayed.

Figure 3:
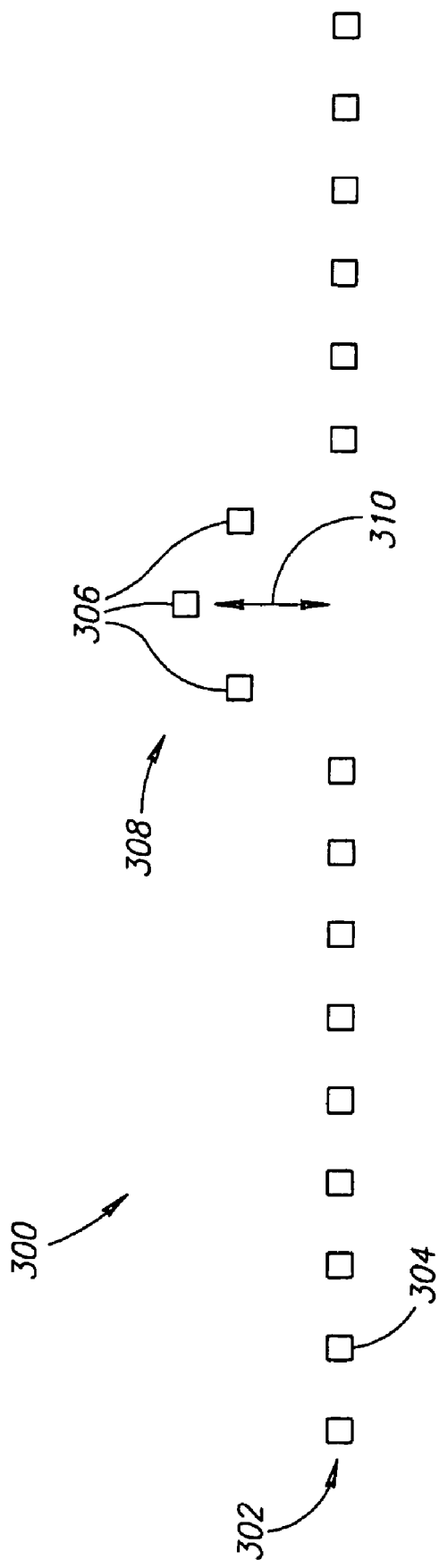
FIG. 3 is a schematic illustration of a pattern format of the patterns displayed to a patient, in accordance with an exemplary embodiment of the invention.

FIG. 3 is a schematic illustration of an exemplary pattern format 300 of the patterns displayed to a patient by system 100. Pattern format 300 comprises a fragmented line 302 formed of a plurality of squares 304, for example between about 10-30 squares (e.g., 27-29). Alternatively, the line 302 has fewer than 10 squares or more than 30 squares. Further alternatively, a continuous line is used. One or more squares 306 (3 squares in FIG. 3) are displaced from line 302, so as to form a distortion 308.

Line 302 optionally has a length which covers between about 10-20° (e.g., 14°) of the patient's visual field, when the patient is situated at a normal distance from screen 12, for example about 30-60 centimeters. It is noted, however, that the tests are valid even if the patient sits much closer to screen 112 or much farther from screen 112. In the following description, whenever a length or distance is stated in degrees it means that the length covers that angle on the patient's visual field under these conditions.

In different displayed patterns, line 302 is displaced from the center of the display, by different distances, so as to cover substantially the entire area covered by the display. In an exemplary embodiment of the invention, line 302 is displaced from the center of the display by different distances up to about −7.0° to 7.0°, depending on the size of the mapped visual field. In larger visual fields larger distances from the center may be used. It is also noted that non-symmetrical distances from the center may be mapped. The different patterns displayed to the patient optionally further differ in the distance (indicated by an arrow 310) between distortion 308 and line 302. The distances 310 of the different patterns are optionally between a maximal distance and a minimal distance. The maximal distance is optionally selected as a distance close to a value so large that it will be identified even by patients with severe lesions. Using larger distances will generally not add information on the patient's visual field. The minimal distance is optionally selected as a distance close to a distortion level that will not be identified by substantially all patients and therefore does not add information on the patient's visual field. In an exemplary embodiment of the invention, the distances 310 used are between about 0.1°-0.35°, although other distances may be used, including distances even up to about 0.8°-2.0° and more.

The different patterns optionally differ in their orientation. In an exemplary embodiment of the invention, in some of the patterns line 302 is horizontal and in other patterns line 302 is vertical. In some embodiments of the invention, diagonal patterns are used, in addition to, and/or instead of, the vertical and horizontal patterns.

The squares 306 forming distortion 308 are optionally curved in the direction opposite the fovea, such that the central square 306 is farther from the fovea than the side squares 306. This distortion direction is similar to the pathological distortion of AMD patients. Alternatively, other shaped distortions are used, including distortions in the direction of the fovea.

Figure 4:
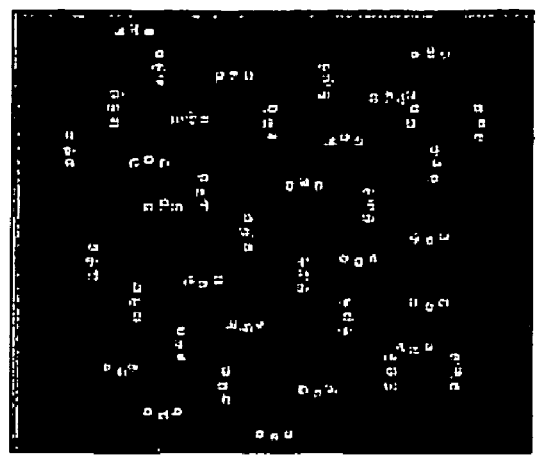
FIG. 4 is a schematic illustration of distortion positions in patterns displayed to a patient in a test session, in accordance with an exemplary embodiment of the invention.

FIG. 4 is a schematic illustration of distortion positions in patterns displayed to a patient in a test session, in accordance with an exemplary embodiment of the invention. It is noted that only a single distortion is displayed at a single time. For clarity, only the distortions are shown, while lines 302 (FIG. 3) are not shown in FIG. 4. A sufficient number of patterns is used in order to cover substantially the entire visual field of the patient in a relatively even distribution. The patterns of FIG. 4 are brought by way of example and substantially any other set of patterns may be used. In some embodiments of the invention, the same set of patterns is used in all tests. Alternatively, different sets of patterns are used for different patients, for different eyes and/or at different times. In some embodiments of the invention, the set of patterns used are selected randomly according to predetermined parameters.

In some embodiments of the invention, the patterns are displayed in a random order, for example in order to prevent patients from memorizing the answers of the test. Alternatively or additionally, the patterns are displayed in an order which begins with distortions which are easier to identify. In some embodiments of the invention, horizontal patterns are displayed before vertical patterns, as most patients detect horizontal patterns more easily. The patterns are optionally ordered in a manner which minimizes the number of changes between substantially different patterns, for example between horizontal and vertical patterns. In some embodiments of the invention, the patterns are arranged in a manner which allows collecting a sufficient amount of data in a first portion of the test session, and continuing to a second portion of the test session only if the early results are non-conclusive. Further alternatively or additionally, the patterns are displayed in an order determined according to any other known considerations of psychophysical tests.

An experimental test sequence suggested for use, is described in U.S. provisional patent application 60/467,562, mentioned above. It is noted, however, that any other set of patterns that sufficiently covers the area of the visual field may be used.

The details of pattern format 300 were presented for illustration purposes and various changes may be made in the pattern format, including the shapes forming line 302, the length of the line and the shape of the distortion. Another option is using short lines of 1°-10°, or long lines of 20°-90°. In some embodiments of the invention, tests are performed even with lines longer than 90° or even longer than 110°. Alternatively or additionally to patterns according to the pattern format in FIG. 3, any other patterns, with or without distortions, may be used, for example the patterns described in U.S. Pat. No. 6,656,131 and/or in PCT patent application PCT/IL03/00135, the disclosures of which are incorporated herein by reference. These references also describe various alternatives to the details of pattern format 300, which may be used in accordance with the invention.

The patterns are optionally displayed for a short period, in a manner which requires the patient to use different areas of the visual field in determining the location of the distortion. Optionally, the view of the patient is fixated to the center of the display before each pattern is displayed, for example by displaying a slowly moving dot from the previously displayed distortion to the center of the display. Alternatively or additionally, a fixation point is displayed in the center of the display and the patient is instructed to fixate to the fixation point. Further alternatively, any other fixation methods known in the art for fixating the patient to the center may be used.

The displaying of the patterns and/or the reception of the indications is optionally performed using any of the embodiments in U.S. Pat. No. 6,656,131 and/or in PCT patent application PCT/IL03/00135.

Referring in detail to giving (206) a score to the patient indication, in some embodiments of the invention, the score is a function of the probability that the patient did not identify the displayed distortion. Optionally, the probability score is a function of the distance between the location of the patient indication and the location of the displayed distortion. This distance is referred to herein as the distance error. In some embodiments of the invention, the probability score is a monotonous function, optionally a non-linear function, which increases with the error distance. In an exemplary embodiment of the invention, system 100 is configured with a lower threshold L1 and an upper threshold L2. The thresholds are optionally configured such that distances below the lower threshold L1 are within a range of commonly made errors of pointing on a well identified distortion. For example, when the pointing is performed after the pattern is removed from the display, such small errors in the pointed location may be due to the patient not remembering the precise location of the distortion and/or due to problems in precise maneuvering of the pointing apparatus. The upper threshold is optionally set such that distances above the upper threshold L2 are only rarely (if at all) due to pointing at a well identified distortion.

In some embodiments of the invention, thresholds L1 and L2 are pre-configured based on tests on a relevant population. In an exemplary embodiment of the invention, L1 is set to 1.5° and L2 is set to 3°. Alternatively, L1 and L2 are adjusted based on the results of the current test. In some embodiments of the invention, L1 and L2 are adjusted according to a comparison of the patient indications to the displayed stimuli. According to the comparison, the error level of the patient is determined and L1 and L2 are set.

Alternatively, L1 and L2 are configured according to preliminary tests performed on the specific patient. Further alternatively, the values of thresholds L1 and L2 used for a specific patient are selected according to the type of pointing apparatus used by the patient and/or the age group (or other group) to which the patient belongs. In some embodiments of the invention, the thresholds L1 and L2 are selected according to the specific tested eye, for example, whether the tested eye is the right or left eye of the patient, whether the tested eye is the dominant eye of the patient and/or whether the tested eye is the first or second eye tested in current session. Further alternatively or additionally, the values of thresholds L1 and/or L2 are adjusted according to the distance from the fovea of the displayed distortion.

For patterns having a distance error of less than L1, a probability score of 0 is optionally assigned. For patterns having a distance error above L2, a score of 1 is optionally assigned. For patterns having a distance error between L1 and L2, the score optionally increases with the distance error. In an exemplary embodiment of the invention, the score increases linearly with the distance error (DE), for example according to score=(DE−L1)/(L2−L1). Alternatively, the score increases according to a non linear function, optionally a monotonous function.

In some embodiments of the invention, the patient may indicate a plurality of locations for a single stimulus. Optionally, if two or more indications closer than a predetermined threshold distance (e.g., 0.5°) are received for a single stimulus, they are considered as a single indication. Optionally, the first or second indication is ignored. Alternatively, each of the indications is given only half the weight of a regular indication. In some embodiments of the invention, when the distance is close to the predetermined threshold distance, each of the indications is given a weight larger than half the weight of a regular indication (for example, 0.7).

Optionally, indications which may be due to a mix up or other mistake are ignored or given low weight. In some embodiments of the invention, for example when a fixation point is used, indications close to the fovea when line 302 passes through the fovea are ignored to prevent mix up due to the fixation point.

Referring in more detail to giving (207) the severity score S, in some embodiments of the invention, the severity score increases linearly with the probability score. Optionally, the severity score increases linearly with the distortion size (ADH). In an exemplary embodiment of the invention, the severity score is equal to the product of the distortion size and the probability score. Alternatively, any other function may be used in calculating the severity score, for example giving more weight to the distortion size. In some embodiments of the invention, other factors are taken into account in generating the severity score, such as the area of the visual field in which the indicated location is situated. For example, distortions in the center of the visual field may be given extra weight in the severity score.

Referring in detail to generating (208) the pattern map M2, in some embodiments of the invention, the map is given a maximal distortion value at the location of the patient indication and lower values surrounding the patient indication location. Thus, the effect of the indication is spread over an area of the visual field of the patient. Optionally, the map is given the severity score at the patient indication location and values decreasing monotonously with the distance, at the locations surrounding the patient indication location (x,y). In an exemplary embodiment of the invention, the value of each of the pixels of map M2 is set by:

$$M2(i,j)=S^*\exp(-d^*(R/\sigma)^2) \quad (1)$$

wherein σ is a Gaussian factor (e.g., 0.75), d is a damping factor (e.g., 0.5) and R is the distance between the position (i,j) and the patient indication (x,y), given for example by $R=\sqrt{(x-i)^2+(y-j)^2}$. Alternatively, R is the distance between the position (i,j) and a projection of the patient indication onto the line of displayed signal. Alternatively to using an exponential decrease in the value of M2 as the distance from the patient indication increases, other functions may be used, such as a polynomial decrease or a linear decrease.

In some embodiments of the invention, map M2 has a different size than a size of a grid on which the patient indication is received. In these embodiments, the patient indications are optionally rescaled onto the grid of map M2, using methods known in the art. The Gaussian factor σ is adjusted accordingly. In an exemplary embodiment of the invention, the rescaling from a grid of 14 points to a grid of fifteen points is performed by multiplying by 50/14.

In order to correct for persistent errors in the patient's indications, in some embodiments of the invention, an error vector representing the persistent error of the patient's indications is determined and pattern map M2 is generated accordingly. Optionally, the distance R used in equation (1) is set to $R=\sqrt{(x-i-x_e)^2+(y-j-y_e)^2}$, wherein $(x_e, y_e)$ is the error vector.

The error vector $(x_e, y_e)$ is optionally determined by accumulating all the patient indications for which there is a high probability that the patient was pointing at the displayed distortion together with the respective locations of the displayed distortions. Alternatively, only some of the indications, most suitable for the calculation of the error vector, are used. The accumulated indications optionally include indications having a distance error smaller than a threshold L3. In an exemplary embodiment of the invention, L3 is equal to L1. In another exemplary embodiment of the invention, L3 is between L1 and L2, for example L3=2. In some embodiments of the invention, L3 is adjusted according to the number of indications accumulated, such that the group of accumulated indications includes at least a minimal number of patient indications, for example at least 3-6 indications. Alternatively, if the group of accumulated indications does not include at least a predetermined number of indications, no adjustment is performed for the persistent errors or additional data is collected so that there is sufficient data for the calculations. The additional data is optionally collected by performing a post-test in which easily identified stimuli are displayed.

The error vector $(x_e, y_e)$ is optionally set as the difference between the average of the location of the accumulated indications and the average of the locations of their respective displayed distortions. Alternatively to using a simple average, a more complex average function may be used, such as an average which does not take into account outliers.

Alternatively to performing the adjustment to the persistent errors in the calculation of maps M2, the locations of the summarized (205) indications are adjusted (204) using the accumulated indications, for example using an affine transform or any other suitable transform which preserves the general spatial relation between the locations of the patient indications.

Alternatively to using the accumulated indications using threshold L3 in determining error vector $(x_e, y_e)$, a preliminary test session is carried out to determine the error vector of the persistent errors of the patient. The preliminary test session is optionally performed immediately before the actual test session, in order to have fresh error vector data. Alternatively, a single preliminary test session is performed for each patient periodically, in order not to add too much burden to the patient.

In the preliminary test session, patterns which are generally not affected by lesions in the visual field, are displayed, for example relatively large patterns and/or patterns displayed for a relatively long duration. In an exemplary embodiment of the invention, dot sizes of about 0.4° are used in the preliminary test session.

Referring in more detail to calculating (210) the accumulative map M1, in some embodiments of the invention, accumulative map M1 is initialized to zero at the beginning of each examination session. For each generated (208) map M2, the accumulated map M1 is updated. Optionally, the value of each pixel (i,j) is set to the sum of the previously accumulated value of the pixel M1(i,j) during the present testing session of the visual field and the value of the pixel in the current map M2(i,j). In some embodiments of the invention, if the sum M1(i,j)+M2(i,j) is above the current severity score S, the value of the accumulated map M1($i,j$) is set to the severity score S. Accordingly, M1 is updated for each new matrix M2 by:

$$\text{New } M1(i, j) = \begin{matrix} M1(i, i) + M2(i, j) & M1(i, j) + M2(i, j) < S \\ S & M1(i, j) + M2(i, j) > S \end{matrix}$$

Alternatively, accumulative map M1 is generated after calculating all of maps M2 and each pixel of M1 is set to the sum of all the corresponding pixels of all of the maps M2 or to the highest severity score S of all the maps M2, whichever is higher.

Referring in more detail to generating (212) the binary map M3, in some embodiments of the invention, a threshold K defines a border between pixel values taken as representing healthy tissue and pixel values taken as representing impaired tissue. The binary map M3 has, without loss of generality, a "zero" value wherever accumulative map M1 has a value beneath threshold K and has a "one" value wherever accumulative map M1 has a value above threshold K.

Optionally, the value of threshold K is selected empirically based on tests in a plurality of patients. In some embodiments of the invention, the value of threshold K is selected based on a desired specificity-sensitivity working point. Optionally, different thresholds K are used for different diseases and/or the specific classification desired. A lower threshold may be used for preliminary disease detection than for determination of a disease stage. In some embodiments of the invention, different values for threshold K are used for patients with different attributes, for example different age groups and/or different disease history. Alternatively or additionally, threshold K is adjusted according to the specific eye of the patient, for example, left/right, first/second tested and/or dominant/non-dominant. In an exemplary embodiment of the invention, a value of between 0.1 and 0.25 is used for K, optionally 0.15.

Referring in detail to identifying (214) clusters, in some embodiments of the invention, a cluster map M4 is generated from binary map M3, using any clustering procedure known in the art, such as K-mean clustering methods and/or morphological image processing methods. In an exemplary embodiment of the invention, a clustering method as described in above mentioned PCT application PCT/IL03/00135 is used, using a proximity criteria between each two points to determine whether they belong to a same cluster.

A final test map M5 is optionally generated from accumulative map M1, masked by cluster map M4. In some embodiments of the invention, the final test map M5 receives the values of accumulative map M1 in those pixels belonging to a cluster in cluster map M4 or binary map M3, while the remaining pixels of final test map M5 are set to 0.

Clustering map M4 optionally indicates for each pixel of accumulative map M1 and final test map M5, whether it belongs to a cluster and/or to which cluster it belongs.

Referring in detail to displaying (220) a map of the visual field, in some embodiments of the invention, accumulative map M1 is displayed. Alternatively or additionally, for simplicity, final map M5, which only shows clusters, is displayed. Further alternatively or additionally, binary map M3 is displayed to give the physician a general view of the possibly afflicted areas.

In some embodiments of the invention, the displaying of non-binary maps (e.g., final map M5), is in accordance with a grayscale coding. Alternatively or additionally, the display uses any other color coding, for example using different colors for different score level ranges. In some embodiments of the invention, the display may receive, for each pixel, a value selected from a multi-value scale including at least three, six, twenty or even above sixty values, allowing a physician to determine the extent and/or severity of the visual field defect at different map locations. In an exemplary embodiment of the invention, the multi-value display scale includes 256 display levels. In some embodiments of the invention, the final map is overlaid on an image of the eye or of other representations of the fundus.

The displayed map is optionally used by a physician to assess the presence of visual field defects in the patient's visual field and the degree and spatial distribution of such defects. In some embodiments of the invention, a physician may compare maps of the visual field of a patient acquired at different times in order to determine trends in progression of lesions in the visual field. The results of the tests in accordance with the present invention may be used together with other tests, such as direct eye examinations. Alternatively, as described above automatic classification of the patient is performed, such that a trained physician is not required in order to provide a classification.

The tests in accordance with embodiments of the invention may be used on different classes of patients. The tests may be performed for AMD screening, for CNV detection or follow up, for example in patients known to have AMD and/or for post photo dynamic therapy (PDT), or any other therapy, follow up. In post PDT patients, the tests may aid in determining if and when re-treatment is required. The tests may also be used for other retinal, chorio-retinal and/or choroidal eye diseases, such as ocular hystoplasmosis, myopia, central serous retinopathy, central serous choroidopathy, glaucoma, diabetic retinopathy, media opacities (such as, but not limited to, cataract), retinitis pigmentosa, optic neuritis, epiretinal membrane, vascular abnormalities and/or occlusions, choroidal dystrophies, retinal dystrophies, macular hole, choroidal or retinal degeneration and/or lens abnormalities.

In some embodiments of the invention, in addition to displaying the map (or instead of displaying the map), other information is displayed, such as the classification of the patient and/or the a confidence of the classification. Optionally, the display includes patient identification information and/or patient medical history. Alternatively or additionally, any other information which may be useful is displayed.

Referring in detail to determining (216) parameters of the impaired clusters, in some embodiments of the invention, the intensity (i.e., the score sum of all the pixels of the cluster) is determined for one or more of the clusters. Optionally, for each of the clusters, the intensity of the cluster is determined by summing the scores of all the pixels classified as belonging to the cluster, in cluster map M4. In some embodiments of the invention, the determined parameters include a maximal intensity (Imax) of any of the clusters. Optionally, the maximal intensity (Imax) parameter is normalized to the area of the pixels of the cluster. The normalization is performed, for example, by multiplying the sum of the cluster having the highest score sum by a normalization factor ($\beta$) determined as the area of the eye represented by map M5 divided by the total number of pixels in map M5.

In an exemplary embodiment of the invention, the tested eye area includes 14°×14°=196 degrees$^2$ and the number of pixels in map M5 is 50×50=2500, such that $\beta$=196/2500.

Alternatively or additionally, the determined (216) parameters include the maximal area of any of the clusters (Amax), for example based on the number of pixels. Further alternatively or additionally, the determined (216) parameters include the maximal score value of a single pixel in the cluster having the largest intensity and/or the cluster having the largest area. Further alternatively or additionally, the determined (216) parameters include the area of the cluster having the greatest intensity and/or the intensity of the cluster having the greatest area. These parameters are indicative of the severity of the damage to a worst state cluster.

In some embodiments of the invention, the determined (216) parameters include the total area of the clusters in map M5 and/or the total number of the clusters. Alternatively or additionally, the parameters may be based on the spatial distribution of the clusters, for example, whether there is a cluster in the center and/or the size of such cluster and/or the shapes of the clusters (e.g., long and narrow or circular). Further alternatively or additionally, the parameters include the width of a boundary area (i.e., an area in which the score is relatively close to the threshold K) of one or more of the clusters and/or a slope of a boundary area. Other parameters which may be used in the classification and/or displayed to the physician include average intensity, the location and/or value of the center of gravity of the cluster and/or the maximal intensity of the cluster.

Referring in detail to classifying (218) the patient, in some embodiments of the invention, tests are performed on a plurality of patients having clear-cut clinical classifications. A function which best correlates between the parameter values of the tested patients and their empirically determined classifications is determined. The patient is classified (218) based on applying the empirically determined function to the determined (216) parameters.

In some embodiments of the invention, the function is generated based on a best selection of sensitivity versus specificity, using any method known in the art. Alternatively, a relatively high specificity or a relatively high sensitivity is used, depending on the specific purpose of the test and/or on the identity of the patient. In some embodiments of the invention, the function used in the classification, depends also on external patient parameters, such as age, patient disease history, ethnic group and/or gender. The function used in the classification optionally depends on the eye being classified, for example whether the eye is the left or right eye, whether the eye is the first or second eye tested in a test session and/or whether the eye is the dominant eye of the patient. The dominant eye of the patient is optionally determined using any method known in the art, or based on the dominant hand of the patient.

In an exemplary embodiment of the invention, the classification (218) is performed by comparing the value of one of the parameters to a threshold which best separates between patients of different classifications. In an exemplary embodiment of the invention, a threshold of Imax=2 is set for the maximal cluster intensity parameter (Imax). Patients having a value equal or above 2 are classified as having CNV, while patients having a value beneath 2 are classified as having intermediate AMD (formerly generally referred to as HRC). These values were selected based on the values shown in table 1. For each patient, a clinical diagnosis was determined without relation to the present invention and the values of parameters Amax and Imax are determined in accordance with the present invention.

According to these tests, using a threshold of Imax=2 achieves a sensitivity of 89.5% and a specificity of 90.9%.

The results are summarized in table 2, which states for each classification (i.e., HRC, CNV), the number of patients having values below of Imax below 2 and the number of patients having a value of Imax above 2.

The classification may also be based on input from a physician viewing the displayed map. In some embodiments of the invention, the map is displayed to a physician with the automatically generated classification and the physician may override the classification if necessary. Optionally, system 100 automatically updates the functions it uses based on corrected classifications, periodically and/or in real time, using supervised or unsupervised learning.

In some embodiments of the invention, the classification is based on other parameters than Imax or Amax, for example any of the parameters mentioned above. Alternatively or additionally, the classification may be based on a comparison of results of a plurality of test sessions over time. For example, the currently determined map may be compared to a previously determined map to determine whether the disease has progressed or not.

Alternatively or additionally to providing a classification, system 100 determines whether additional tests are needed and if so which tests are to be performed. The additional tests may be similar to the originally performed tests but with different parameter values. The additional tests may be concentrated in specific regions of the visual field of the patient. Alternatively or additionally, the additional tests may use different shapes of patterns, for example when the previously used pattern format did not provide conclusive results. Alternatively or additionally, the additional tests may relate to other areas of the eye which were not tested sufficiently.

TABLE 1

| Patient No. | Clinical patient Diagnosis | $A_{max}$ | $I_{max}$ |
|---|---|---|---|
| 1 | HRC | 0 | 0 |
| 2 | HRC | 0 | 0 |
| 3 | HRC | 0.39200002 | 0.049400505 |
| 4 | HRC | 0.862399995 | 0.113490924 |
| 5 | HRC | 1.646399975 | 0.244715348 |
| 6 | HRC | 2.11680007 | 0.315895557 |
| 7 | HRC | 2.273600101 | 0.382590175 |
| 8 | HRC | 2.90079999 | 0.491386235 |
| 9 | HRC | 3.763200045 | 0.585396945 |
| 10 | HRC | 3.449599981 | 0.639674544 |
| 11 | HRC | 3.528000116 | 0.643468916 |
| 12 | HRC | 3.763200045 | 0.68581444 |
| 13 | CNV | 4.939199924 | 0.717079818 |
| 14 | CNV | 5.174399853 | 0.878878891 |
| 15 | HRC | 6.115200043 | 0.917004526 |
| 16 | HRC | 5.801599979 | 0.950332046 |
| 17 | HRC | 5.252799988 | 0.960393012 |
| 18 | HRC | 5.331200123 | 1.098310947 |
| 19 | HRC | 7.291200161 | 1.183715463 |
| 20 | HRC | 7.291200161 | 1.188845992 |
| 21 | HRC | 7.291200161 | 1.622310638 |
| 22 | HRC | 8.232000351 | 1.800713181 |
| 23 | CNV | 11.99520016 | 2.404366493 |
| 24 | CNV | 13.64160061 | 2.60819459 |
| 25 | HRC | 13.40639973 | 2.87279582 |
| 26 | CNV | 20.07040024 | 3.532650948 |
| 27 | CNV | 16.54240036 | 3.583990812 |
| 28 | CNV | 24.85280037 | 4.282537937 |
| 29 | CNV | 25.47999954 | 4.831693172 |
| 30 | CNV | 28.22400093 | 5.313684464 |
| 31 | CNV | 26.81279945 | 5.649202824 |
| 32 | HRC | 28.30240059 | 5.878853798 |
| 33 | CNV | 64.44480133 | 10.86080837 |
| 34 | CNV | 65.15039825 | 13.65911961 |
| 35 | CNV | 61.23040009 | 13.80097485 |
| 36 | CNV | 79.57600403 | 16.34333611 |
| 37 | CNV | 79.57600403 | 18.61971283 |
| 38 | CNV | 84.82880402 | 19.08659935 |
| 39 | CNV | 87.96479797 | 19.58306885 |
| 40 | CNV | 128.7328033 | 28.28132439 |
| 41 | CNV | 122.3824005 | 29.0915966 |

TABLE 2

|  | HRC | CNV | total |
|---|---|---|---|
| Imax < 2 | 20 | 2 | 22 |
| Imax > 2 | 2 | 17 | 19 |
| Total | 22 | 19 | 41 |

In some embodiments of the invention, system 100 analyzes the test data of the patient din order to provide further testing and/or treatment related suggestions. Optionally, the patient is tested a plurality of times and the results of the different tests are compared for the further testing and/or treatment related determination.

Optionally, system 100 suggests a time at which another test is to be performed. In some embodiments of the invention, system 100 automatically reminds the patient to perform the tests and/or provides a physician with a list of patients that did not perform the tests on time. The next time to perform the test is optionally determined according to the rate of change from a previous test to the current test. The rate of change is optionally determined by determining a change amount divided by the time between the two tests. When the rate of change is relatively fast, more frequent test sessions are optionally suggested.

In some embodiments of the invention, the values of the cluster intensity parameter Imax from a plurality of test sessions of the eye is fit into a model of the expected behavior of the parameter over time. For example, after PDT eye treatment, the parameter is expected to behave according to a parabolic model over time. The parameter first decreases and then begins to increase. Additional treatment is to be performed at the minimum of the parabola. Based on the fitting of the parameter values into the model, an expected time at which the minimum will be reached is determined and accordingly a time for a next test session is set. Alternatively, a time at which the minimum will be or was reached is determined and accordingly a treatment session is set.

Alternatively, the values of other parameters may be fit into the model. In some embodiments of the invention, whether additional treatment is required is determined for the slope of the change of the parameter value. Alternatively or additionally, the type of treatment is determined. For example, the tests may be used to determine whether to use laser treatment, PDT or drug injection.

It is noted that tests in accordance with the present invention may be relatively simple and optionally require only a few minutes (e.g., 5 minutes) per eye. Furthermore, the tests may be performed in a patient's home. The tests may be performed frequently, for example, every week or even every 2-3 days. Thus, the tests of the invention can be used for frequent monitoring of neovascular AMD patients, regardless of whether they underwent treatment.

Following is a description of a study performed on patients that underwent PDT treatment.

Thirteen patients with diagnosed sub-foveal CNV were subjected to standard visual acuity (VA) and fluorescein Angiography (FA) tests, before PDT treatment. In addition, the patients underwent a test in accordance with an embodiment of the present invention (referred to herein as PHP. The patients then underwent PDT treatment. Twelve weeks after the PDT treatment, the patients were subjected to the same three tests.

TABLE 3

| Patient Number | VA | FA | PHP |
|---|---|---|---|
| 1 | Deteriorated | Deteriorated | Deteriorated |
| 2 | Deteriorated | Deteriorated | Deteriorated |
| 3 | Deteriorated | Deteriorated | Deteriorated |
| 4 | Deteriorated | Stable | Deteriorated |
| 5 | Stable | Improved | Improved |
| 6 | Stable | Improved | Improved |
| 7 | Stable | Improved | Improved |
| 8 | Stable | Stable | Improved |
| 9 | Stable | Stable | Improved |
| 10 | Stable | Stable | Stable |
| 11 | Improved | Improved | Improved |
| 12 | Improved | Improved | Improved |
| 13 | Improved | Improved | Improved |

The results of the tests pre and post PDT treatment were compared. The FA test results were evaluated by a retina specialist. The PHP results were visually examined and the total area of the cluster(s) in the maps M5 were visually estimated. The results are given in TABLE 3.

The results shown in TABLE 3 may be summarized as follows:

In 7 patients (53% of total patient number), the PHP correlated with both FA and VA. In 4 patients (31%), the PHP correlated either with VA (in cases in which the FA results were stable) or with FA (in cases in which the VA results were stable). In 2 patients (16%) the PHP results showed improvement while VA and FA test results did not demonstrate any change.

Figure 5:
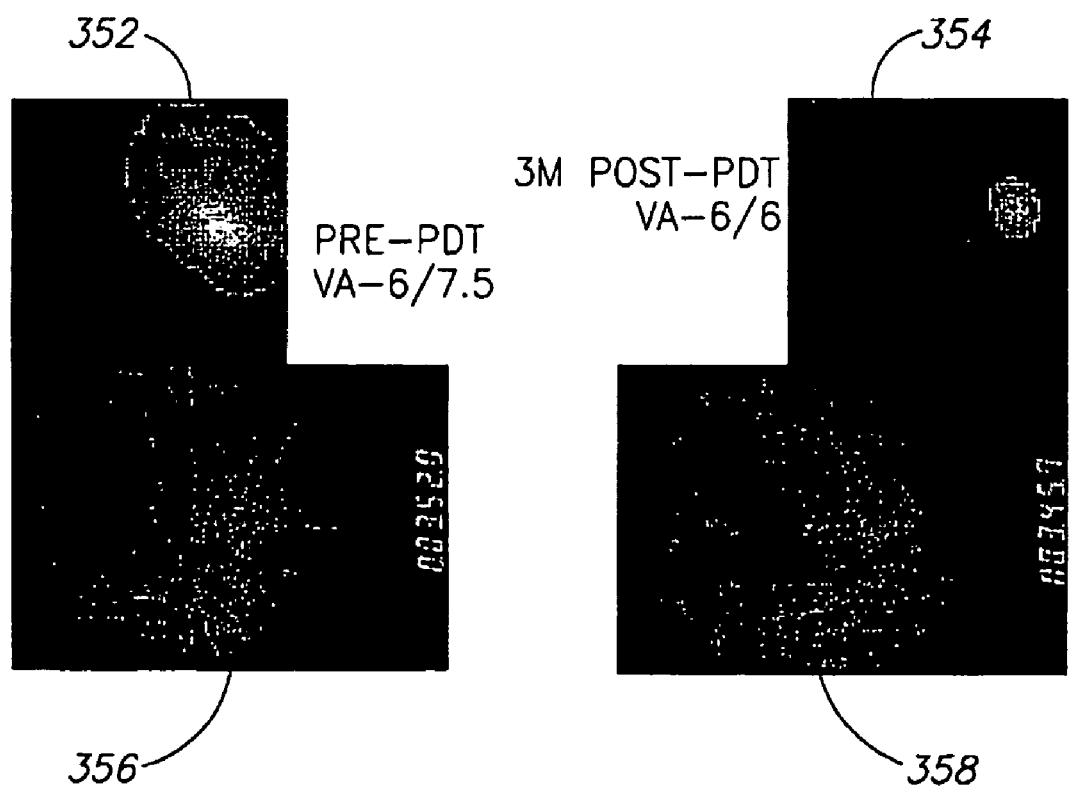
FIG. 5 is a composite image illustrating PHP and FA test results of a patient, before and after PDT treatment.

FIG. 5 is a composite image illustrating PHP and FA test results of a patient, before and after PDT treatment. Images 352 and 354 show the final map M5 of the same patient taken before PDT treatment (image 352) and three months after the PDT treatment (354). Images 356 and 358 are corresponding FA photographs of the retina of the same tested eye taken before PDT treatment (356) and three months after the PDT treatment (358). The VA results for the same patient were 6/7.5 before PDT treatment and 6/6 after PDT treatment. FIG. 5 thus illustrates a good correlation between the FA, VA and PHP test results performed pre-PDT and post-PDT in the same eye.

The PDT study results show a good correlation between the results of PHP, FA and VA tests. Furthermore, the results show a possibility that the PHP test is more sensitive than VA and FA for post-PDT changes.

Figure 6:
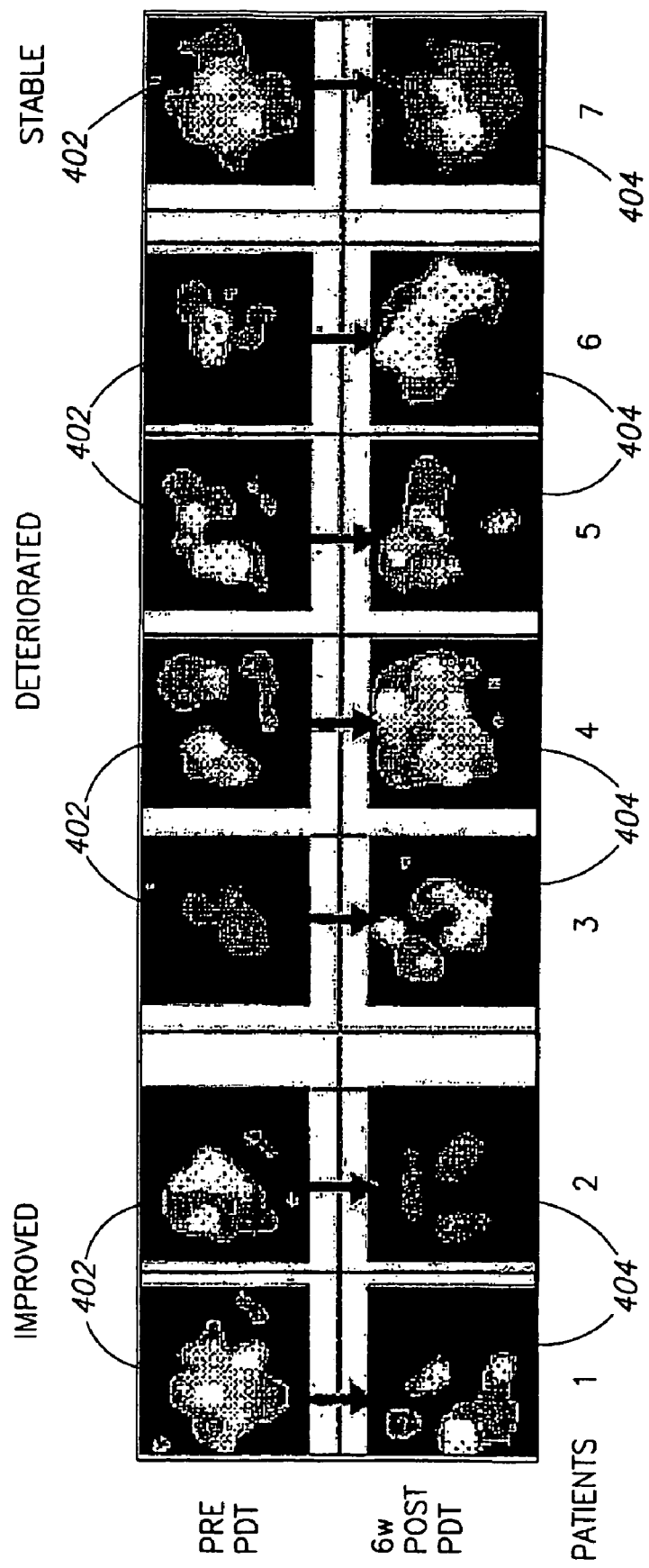
FIG. 6 shows a comparison of final maps M5 of seven patients, in tests performed before PDT treatment and six weeks after PDT treatment, in accordance with an exemplary embodiment of the invention.

FIG. 6 shows a comparison of final maps M5 of seven patients, in tests performed before PDT treatment and six weeks after PDT treatment, in accordance with an exemplary embodiment of the invention. For each of the patients, a map 402 shows the test results before the PDT treatment and a map 404 shows the test results six weeks after the PDT treatment, in the same eye.

The maps 402 and 404 in columns 1 and 2 show improvement after the PDT treatment. The maps in columns 3, 4, 5 and 6 show deterioration after the PDT treatment and the maps in column 7 show stability. These maps show that the functionality of the patient's visual field may change within short periods. In addition, the functional testing of the present invention, may offer in some cases, a better and more consistent resolution in time, than the anatomical FA test, known in the art.

In the above description, the patient indications indicate locations on a relatively large grid. Alternatively, for simplicity, the visual field is divided into a plurality of sectors and the score of each indication is accumulated in a sector score of the sector including the location of the received indication. Sectors having a high score are considered affected by a lesion. The patient is optionally classified according to a maximal sector score.

In some embodiments of the invention, the sectors have square or round shapes or other shapes that have close to equal width and length. Alternatively, the sectors have long and narrow shapes, such as rectangular strips. Further alternatively, the sectors have triangular shapes, rings or circular sector shapes.

In the above description, each displayed stimulus includes a pattern with a visual distortion effecting the shape of the pattern. It is noted, however, that other defects in the pattern may be used including a gap (i.e., a missing portion) in the pattern, a color change in the pattern and/or a blurring of the pattern. In some embodiments of the invention, additional stimuli may be used to further detract the patient from the pattern, and thus cause the patient to identify vision field lesions rather than the displayed defects. For example, a sound stimulus may be used for the detraction.

Alternatively to using stimuli with defects, stimuli to be identified themselves (not defects) by the patient are used. When a stimulus is not identified by the patient, the location of the displayed stimulus is assumed to be defected. The test results are summarized by the amplitude of the displayed stimulus, the location of the displayed stimulus and whether the stimulus was identified by the patient.

It will be appreciated that the above described methods may be varied in many ways. It should also be appreciated that the above described description of methods and apparatus are to be interpreted as including apparatus for carrying out the methods and methods of using the apparatus. The apparatus of the present invention may be implemented in hardware, software or a combination thereof. The present invention includes software for carrying out the methods described above, storage media storing such software and apparatus running the software.

The present invention has been described using non-limiting detailed descriptions of embodiments thereof that are provided by way of example and are not intended to limit the scope of the invention. For example, the processing in FIG. 2 may be performed for each patient indication upon reception of the indication, or may be performed after all the indications of a session or a portion of a session were received. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

The invention claimed is:

1. Apparatus for eye diagnosis, comprising:
    a display unit for projecting stimuli on a patient retina at least some of the projected stimuli comprise defects having varying defect amplitudes;
    an input interface for receiving indications from a patient responsive to the displayed stimuli;
    a processor adapted to generate a map of the patient's visual field, responsive to patient indications relating to the stimuli received by the input interface, and to determine whether the patient has a specific stage of age-related macular disease responsive to the map; and
    an output interface for providing a human tangible indication of a result of the determination.

2. Apparatus according to claim 1, wherein the display unit comprises a screen for displaying stimuli to a patient.

3. Apparatus according to claim 1, wherein the display unit comprises an eye projector for displaying stimulus on a patient's eye.

4. Apparatus according to claim 1, wherein the processor is remote from the input interface.

5. Apparatus according to claim 1, wherein the processor is adapted to determine a cluster parameter of a cluster on said map and to classify the patient with regard to an eye disease, at least partially based on said cluster parameter.

6. Apparatus according to claim 1, wherein the processor is adapted to suggest a time at which to perform treatment.

7. Apparatus according to claim 1, wherein the processor is adapted to suggest a type of treatment to be used.

8. Apparatus according to claim 1, wherein the processor is adapted to suggest whether to perform treatment.

9. Apparatus according to claim 1, wherein the processor is adapted to display the generated map.

10. Apparatus according to claim 1, wherein the processor is adapted to generate the map based on indications received in response to a plurality of consecutively displayed patterns.

11. Apparatus according to claim 1, wherein the processor is adapted to generate the map not primarily based on the contrast of the displayed stimuli.

12. Apparatus according to claim 1, wherein the processor is adapted to generate the map responsive to patient indications received by the input interface relating to shape information on the stimuli.

13. Apparatus according to claim 1, wherein the processor is adapted to generate the map responsive to patient indications received by the input interface relating to locations of distortions in the displayed stimuli.

14. Apparatus according to claim 1, wherein the processor is adapted to generate the map responsive to patient indications received by the input interface relating to whether displayed patterns are perceived with distortions.

15. Apparatus according to claim 1, wherein the processor is adapted to generate the map responsive to patient indications relating to which of a plurality of shapes is most similar to a displayed pattern.

16. Apparatus according to claim 1, wherein the processor is adapted to generate the map without using received indications relating to displayed patterns that have a high probability of not being perceived by the patient.

17. A method of providing an eye diagnosis, comprising:
    displaying stimuli to a patient;
    receiving indications from a patient responsive to the displayed stimuli;
    providing an indication of the eye of the patient with which the patient viewed the displayed stimuli in receiving the indications;
    selecting a classification method from a plurality of different classification methods based on the provided indication of the eye with which the patient viewed the displayed stimuli; and
    classifying the patient with regard to an eye disease, using the selected classification method.

18. A method according to claim 17, wherein providing the indication comprises providing the indication before displaying the stimuli.

19. A method according to claim 17, wherein providing the indication comprises providing the indication after displaying at least some of the stimuli.

20. A method according to claim 17, wherein providing the indication comprises providing the indication by the patient.

21. A method according to claim 17, wherein providing the indication comprises providing the indication by an apparatus performing the display in the form of an instruction to the patient.

22. A method according to claim 17, wherein providing the indication comprises providing an indication as to whether the eye is a right eye or a left eye.

23. A method according to claim 17, wherein providing the indication comprises providing an indication as to whether the eye with which the patient viewed the displayed stimuli is a first or second eye tested in a test session.

24. A method according to claim 17, wherein providing the indication comprises providing an indication as to whether the eye with which the patient viewed the displayed stimuli is a dominant eye of the patient.

25. A method according to claim 17, wherein the plurality of classification methods differ in a threshold to which a final score is compared.

26. A method of providing an eye diagnosis, comprising:
displaying stimuli to a patient at least some of the displayed stimuli comprise defects having varying defect amplitudes;
receiving indications from a patient responsive to the displayed stimuli;
associating the received indications with locations in the visual field of the patient;
determining a translation of the associated locations of the received indications due to persistent errors in the patient's perception or pointing behavior, responsive to at least some of the received indications; and
generating a map of the visual field of the patient responsive to the received indications, as corrected by the determined translation.

27. A method according to claim 26, wherein the persistent errors are determined responsive to indications received before or after a current test session.

28. A method according to claim 26, wherein the persistent errors are determined responsive to indications received during a current test session.

29. A method according to claim 28, wherein the persistent errors are determined responsive to indications provided by the patient at locations close to defects of the displayed stimuli.

30. A method according to claim 26, wherein said translation is achieved by applying an affine transform to the indications.

31. A method of providing an eye diagnosis, comprising:
displaying stimuli to a patient, at least some of the displayed stimuli comprise defects having varying defect amplitudes;
receiving input indications from the patient regarding the displayed stimuli;
generating a visual field map of an eye responsive to the received input indications;
analyzing the visual field map, automatically by a processor, so as to generate an indication of whether the patient has a specific stage of age-related macular disease; and
providing, by the processor, a human-tangible output of the generated indication.

32. A method according to claim 31, wherein all the stimuli displayed in said step of displaying stimuli have the same contrast level.

33. A method according to claim 31, wherein displaying the stimuli comprises displaying consecutively a plurality of patterns.

34. A method according to claim 31, wherein providing the indication comprises providing an indication on whether the patient has wet age-related macular disease.

35. A method according to claim 31, wherein providing the indication comprises providing an indication on whether the patient has an intermediate age-related macular disease stage.

36. A method according to claim 31, wherein providing the indication comprises providing an indication on whether the patient has a different stage of AMD relative to a previous diagnosis session.

37. A method according to claim 31, wherein receiving the indications comprises receiving indications of locations of perceived distortions in the displayed stimuli.

38. A method according to claim 31, wherein receiving said input indications comprises receiving indications of whether a displayed pattern includes a distortion.

39. A method according to claim 31, wherein receiving said input indications comprises receiving regarding one or more displayed patterns an indication of which of a plurality of shapes is most similar to the displayed pattern.

40. A method according to claim 31, wherein generating said visual field map comprises ignoring input indications that are determined to have a high probability of being incorrect due to low sensitivity of the patient's sight.

41. A method according to claim 31, wherein receiving the input indications from the patient comprises receiving indications regarding the shape of the displayed stimuli.

42. A method according to claim 33, wherein the displayed patterns have a plurality of different shapes.

43. A method according to claim 31, wherein at least some of the received indications represent positions at which the patient believes to have perceived defects in said stimuli.

44. A method according to claim 43, wherein generating the map comprises determining, for each indication, a distance between the indication and the respective displayed defect and determining a weight of specific indications in the spatial analysis according to the distance between the indications and the displayed defects.

45. A method according to claim 43, wherein displaying the patterns with defects comprises displaying defects of different amplitudes and giving higher weight to indications corresponding to larger defects.

46. A method according to claim 43, wherein the defects comprise spatial distortions or gaps of missing portions of the patterns.

47. A method according to claim 31, wherein displaying the stimuli comprises displaying patterns and wherein the received indications represent positions at which the patient believes to have identified distortions in said patterns.

48. A method according to claim 31, wherein generating the map comprises generating such that at least some of the indications affect pixels of the map other than the pixel corresponding to the received indication.

49. A method according to claim 31, wherein generating the map comprises generating such that at least some of the indications affect an area of the map larger than the area covered by the indication.

50. A method according to claim 31, wherein generating the map comprises generating such that at least some of the indications affect a plurality of pixels on the map.

51. A method according to claim 31, wherein generating the map comprises assigning each pixel a value at least partially representative of a severity of the malfunctioning of a corresponding area of the patient's visual field.

52. A method according to claim 31, wherein generating the map comprises assigning each pixel a value at least partially representative of a probability that a corresponding area of the patient's visual field is abnormal.

53. A method according to claim 31, comprising determining on the generated map at least one cluster of values corresponding to abnormal tissue.

54. A method according to claim 53, wherein the at least one cluster comprises a plurality of clusters and comprising determining a largest cluster of the plurality of clusters.

55. A method according to claim 54, comprising determining a parameter of the largest cluster.

56. A method according to claim 55, wherein determining the parameter of the largest cluster comprises determining a size-related parameter different from a parameter used in selecting the largest cluster.

57. A method according to claim 55, wherein determining the parameter of the largest cluster comprises determining a size-related parameter used in selecting the largest cluster.

58. A method according to claim 55, wherein determining the parameter comprises determining a plurality of parameters.

59. A method of providing an eye diagnosis, comprising:
displaying stimuli to a patient, wherein all the stimuli presented to said patient within a test session have the same contrast level;
receiving indications from the patient regarding the stimuli;
generating a visual field map of an eye responsive to the received indications;
analyzing the visual field map, automatically by a processor, so as to generate an indication of whether the patient has a specific stage of age-related macular disease; and
providing, by the processor, a human-tangible output of the generated indication.

60. Apparatus for eye diagnosis, comprising:
a display unit for projecting stimuli on a patient's retina;
an input interface for receiving indications from a patient responsive to the displayed stimuli;
a processor adapted to control said display unit for presenting, for a first duration, a test pattern to said patient, to allow the patient to form a perceived image of said test pattern, for receiving from said patient, input indications indicative of a difference between said perceived image and the test pattern, if said patient perceived a difference, said presenting and receiving being repeated one or more times, wherein for at least one of the repetitions said patient is subjected to a competing sensory stimulus, for analyzing the received input indications to determine quantitative information on the vision of said patient, wherein the analysis is at least partially responsive to one or more characteristics of said competing sensory stimulus, said processor is adapted to generate a map of the patient's visual field, responsive to said quantitative information, and to determine whether the patient has a specific stage of age-related macular disease responsive to the map; and
an output interface for providing a human tangible indication of a result of the determination.

61. The apparatus according to claim 60 wherein said competing sensory stimulus comprises an artificially distorted test pattern having a distortion amplitude.

62. The apparatus according to claim 61 wherein said at least one repetition comprises a plurality of repetitions and wherein said distortion amplitude varies for different repetitions of said artificially distorted test pattern.

63. The apparatus according to claim 60, wherein the received indications represent positions at which the patient believes to have identified distortions in said test patterns patterns.

64. The apparatus according to claim 60, wherein generating said map comprises generating said map such that at least some of the indications affect pixels of the map other than the pixel corresponding to the received indication.

65. The apparatus according to claim 60, wherein generating said map comprises generating said map such that at least some of the indications affect an area of the map larger than the area covered by the indication.

66. The apparatus according to claim 60, wherein generating said map comprises generating said map such that at least some of the indications affect a plurality of pixels on the map.

67. The apparatus according to claim 60, wherein generating said map comprises assigning each pixel of said map a value at least partially representative of a severity of the malfunctioning of a corresponding area of the patient's visual field.

68. The apparatus according to claim 60, wherein generating said map comprises assigning each pixel of said map a value at least partially representative of a probability that a corresponding area of the patient's visual field is abnormal.

69. The apparatus according to claim 60, wherein said processor is adapted to determine on the generated map at least one cluster of values corresponding to abnormal tissue.

70. The apparatus according to claim 69, wherein the at least one cluster comprises a plurality of clusters and comprising determining a largest cluster of the plurality of clusters.

71. The apparatus according to claim 70, wherein said processor is adapted for determining at least one parameter of said largest cluster.

72. The apparatus according to claim 71, wherein said determining at least one parameter of the largest cluster comprises determining a size-related parameter different from a parameter used in selecting the largest cluster.

73. The apparatus according to claim 71, wherein said determining at least one parameter of the largest cluster comprises determining a size-related parameter used in selecting the largest cluster.

74. The apparatus according to claim 71, wherein said determining at least one parameter comprises determining a plurality of parameters of said largest cluster.

75. A method of providing an eye diagnosis of a patient, comprising:
presenting, for a first duration, a test pattern to said patient, to allow the patient to form a perceived image of said test pattern;
receiving from said patient, input indicative of a difference between said perceived image and the test pattern, if said patient perceived a difference, said presenting and receiving being repeated one or more times, wherein for at least one of the repetitions said patient is subjected to a competing sensory stimulus;
analyzing the received input to determine quantitative information on the vision of said patient, wherein the analysis is at least partially responsive to one or more characteristics of said competing sensory stimulus;
generating a visual field map of an eye responsive to said quantitative information;

analyzing the visual field map, automatically by a processor, so as to generate an indication of whether the patient has a specific stage of age related macular disease; and providing, by the processor, a human-tangible output of the generated indication.

76. The method according to claim 75 wherein said competing sensory stimulus comprises an artificially distorted test pattern having a distortion amplitude.

77. The method according to claim 75 wherein said at least one repetition comprises a plurality of repetitions and wherein said distortion amplitude varies for different repetitions of said artificially distorted test pattern.

78. The method according to claim 75, wherein the received indications represent positions at which the patient believes to have identified distortions in said test patterns.

79. The method according to claim 75, wherein generating said map comprises generating said map such that at least some of the indications affect pixels of the map other than the pixel corresponding to the received indication.

80. The method according to claim 75, wherein generating said map comprises generating said map such that at least some of the indications affect an area of the map larger than the area covered by the indication.

81. The method according to claim 75, wherein generating said map comprises generating said map such that at least some of the indications affect a plurality of pixels on the map.

82. The method according to claim 75, wherein generating said map comprises assigning each pixel of said map a value at least partially representative of a severity of the malfunctioning of a corresponding area of the patient's visual field.

83. The method according to claim 75, wherein generating said map comprises assigning each pixel of said map a value at least partially representative of a probability that a corresponding area of the patient's visual field is abnormal.

84. The method according to claim 75, further comprising determining on the generated map at least one cluster of values corresponding to abnormal tissue.

85. The method according to claim 84, wherein the at least one cluster comprises a plurality of clusters and comprising determining a largest cluster of the plurality of clusters.

86. The method according to claim 85, comprising determining at least one parameter of said largest cluster.

87. The method according to claim 86, wherein said determining at least one parameter of the largest cluster comprises determining a size-related parameter different from a parameter used in selecting the largest cluster.

88. The method according to claim 86, wherein said determining at least one parameter of the largest cluster comprises determining a size-related parameter used in selecting the largest cluster.

89. The method according to claim 86, wherein said determining at least one parameter comprises determining a plurality of parameters of said largest cluster.

90. A method of providing an eye diagnosis, comprising:
consecutively presenting to a patient a plurality of test stimuli, to allow the patient to form a perceived image of said test stimuli, at least some of the presented test stimuli include artificially introduced competing stimuli having varying competing stimuli amplitudes, wherein said competing stimuli are adapted to compete with said patient's perception of a pathology related changes in the presented test stimuli;

determining from input indications provided by said patient in response to the presentation of said stimuli a plurality of quantitative values representing the severity of the pathology related changes perceived by said patient in response to said stimuli; and generating a visual field map of an eye responsive to said quantitative values.

91. The method according to claim 90 further comprising automatically analyzing said visual field map, by a processor, so as to generate an indication of whether said patient has a specific stage of age related macular disease; and providing, by said processor, a human-tangible output of the generated indication.

92. The method according to claim 90, wherein said stimuli comprise test patterns and said competing stimuli comprise distortions having varying distortion amplitudes introduced into said test patterns.

93. The method according to claim 92, wherein the input indications received from said patient represent positions at which said patient believes to have identified distortions in said test patterns.

94. Apparatus for providing an eye diagnosis, comprising:
a display unit for projecting a plurality of test stimuli on a patient's retina;

an input interface for receiving indications from said patient responsive to the displayed stimuli;

a processor adapted to control said display unit for consecutively presenting to said patient a plurality of said test stimuli, to allow the patient to form a perceived image of said test stimuli, at least some of the presented test stimuli include artificially introduced competing stimuli having varying competing stimuli amplitudes, said competing stimuli are adapted to compete with said patient's perception of a pathology related changes in the presented test stimuli, said processor is adapted for determining from said input indications a plurality of quantitative values representing the severity of the pathology related changes perceived by said patient in response to said stimuli and for generating a visual field map of an eye of said patient responsive to said quantitative values.

95. The apparatus according to claim 94 wherein said processor is adapted for automatically analyzing said visual field map to generate an output indication of whether said patient has a specific stage of age related macular disease and for providing a human-tangible output of the generated output indication.

96. The apparatus according to claim 94, wherein said stimuli comprise test patterns and said competing stimuli comprise distortions having varying distortion amplitudes introduced by said processor into said test patterns.

97. The apparatus according to claim 96, wherein said input interface is adapted for receiving from said patient input indications representing positions at which said patient believes to have identified distortions in said test patterns.

* * * * *